United States Patent [19]

Lovoi et al.

[11] Patent Number: 4,588,885

[45] Date of Patent: May 13, 1986

[54] METHOD OF AND APPARATUS FOR THE REMOVAL OF PAINT AND THE LIKE FROM A SUBSTRATE

[75] Inventors: Paul A. Lovoi, Saratoga; Alan M. Frank, Livermore, both of Calif.

[73] Assignee: International Technical Associates, Santa Clara, Calif.

[21] Appl. No.: 577,760

[22] Filed: Feb. 7, 1984

[51] Int. Cl.$^4$ .............................................. G01N 21/27
[52] U.S. Cl. ..................... 250/226; 250/205; 134/38; 219/121 LB; 356/328
[58] Field of Search ................. 250/205, 226; 134/38; 219/121 L, 121 LA, 121 LB, 121 LE, 121 LF, 121 LG, 121 LH; 356/72, 326, 328

[56] References Cited

U.S. PATENT DOCUMENTS

| | | | |
|---|---|---|---|
| 3,700,850 | 10/1972 | Lumley et al. | 219/121 LB |
| 4,176,946 | 12/1979 | Takahashi | 250/226 |
| 4,381,894 | 5/1983 | Gogol, Jr. et al. | 356/72 |

Primary Examiner—Edward P. Westin
Attorney, Agent, or Firm—Thomas M. Freiburger

[57] ABSTRACT

A method and apparatus for controlling the stripping of paint and the like from a substrate is disclosed. Embodiments for controlling the stripping of paint and the like by pulses of high intensity radiant energy are described. The control is accomplished by illuminating the area of the paint and the like which is to be stripped and subjecting the light reflected therefrom to spatial spectral dispersion. The spatial spectral dispersion is sensed and an electronic signal representative thereof is generated. The generated electronic signal is compared to a prerecorded electronic signal representative of the spatial spectral dispersion of light reflected from the paint and the like which is to be stripped before each pulse of high intensity radiant energy and the pulse is applied only upon such comparison resulting in a substantial match. Methods and means for normalization of the sensed spatial spectral dispersion and for utilizing mismatch comparisons are disclosed.

10 Claims, 6 Drawing Figures

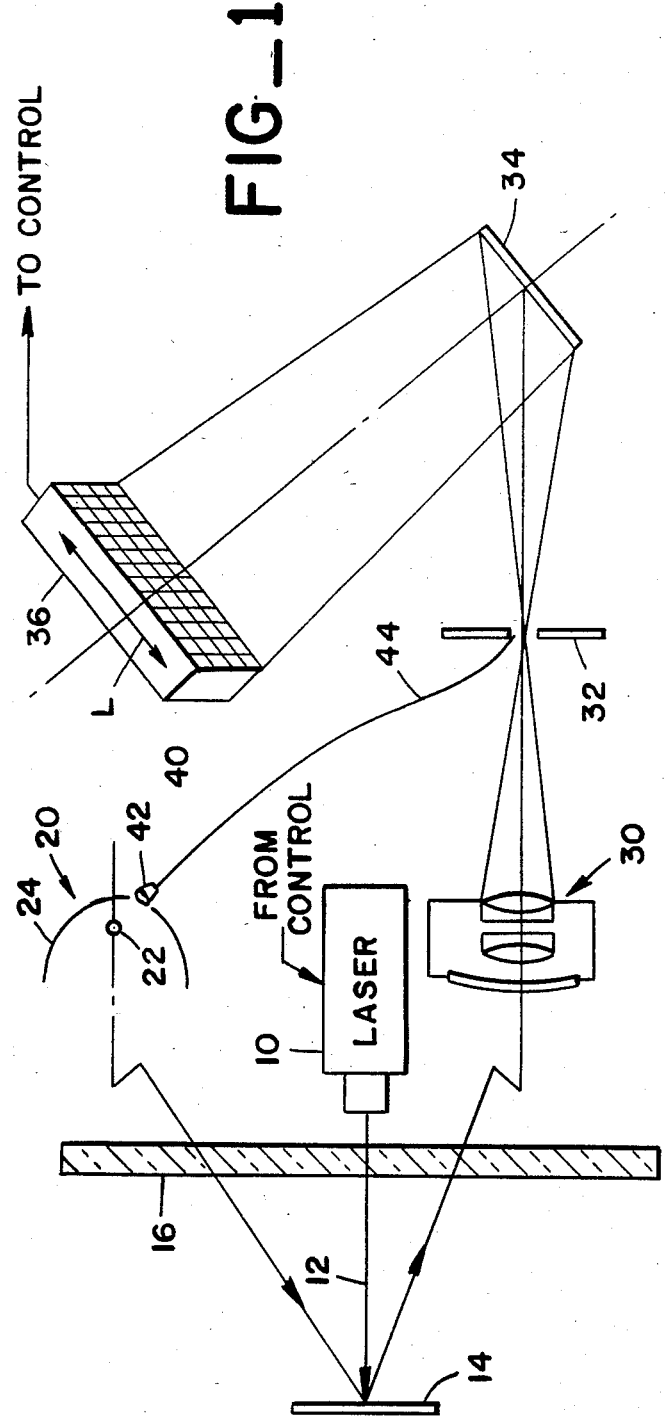
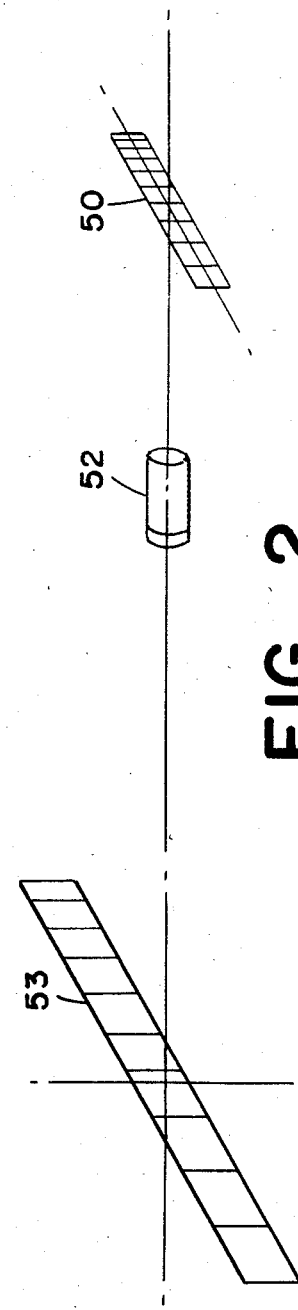

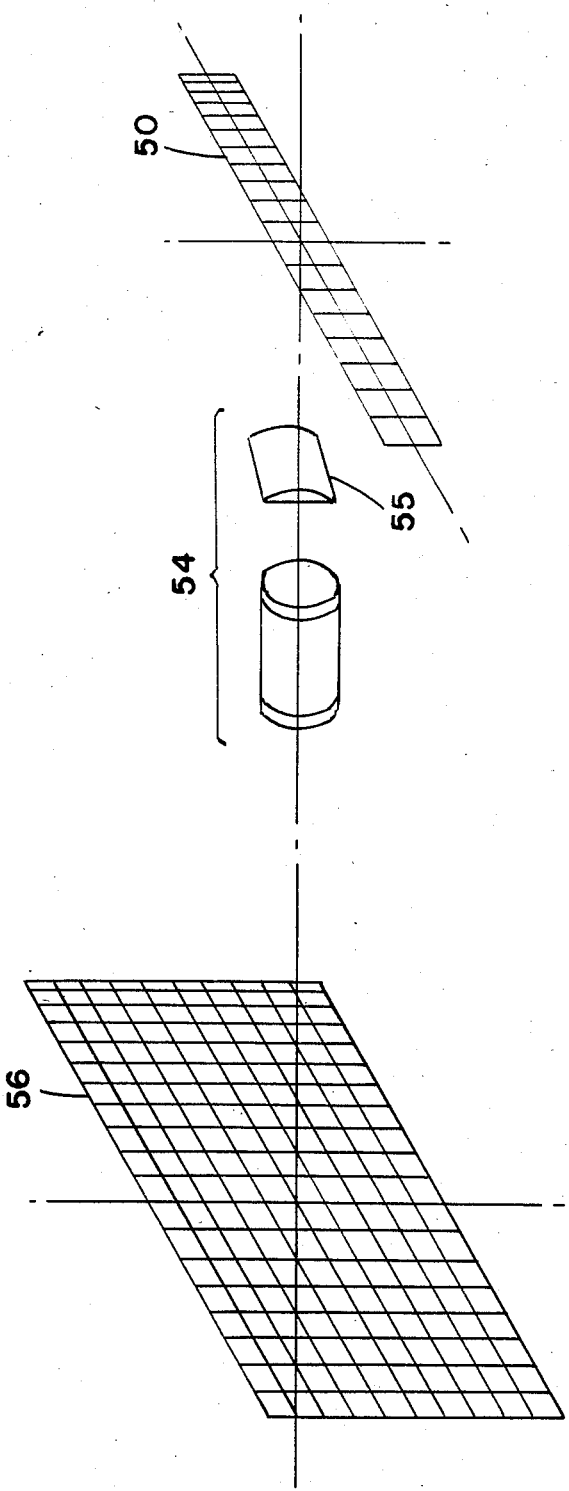
FIG_3

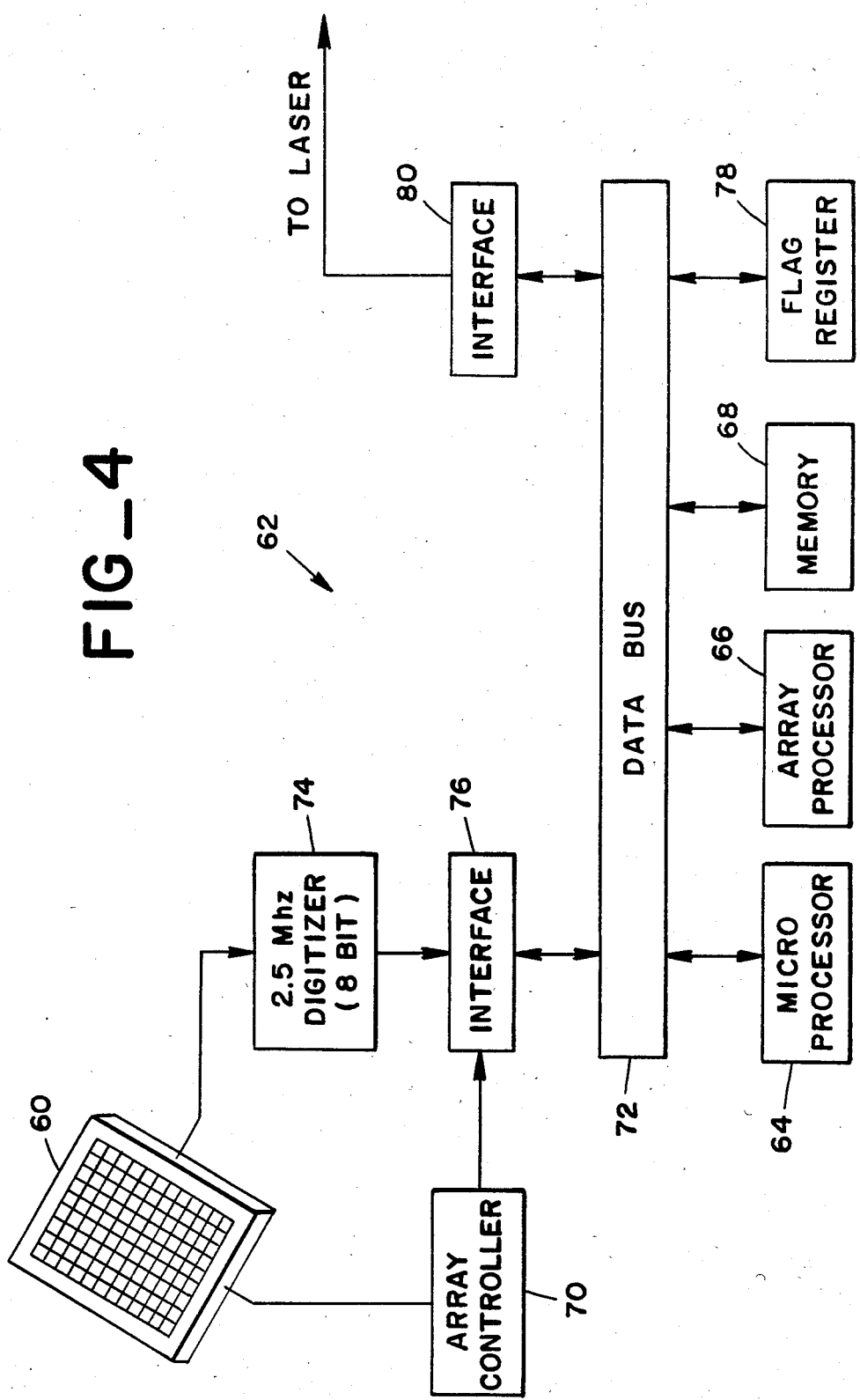
FIG_4

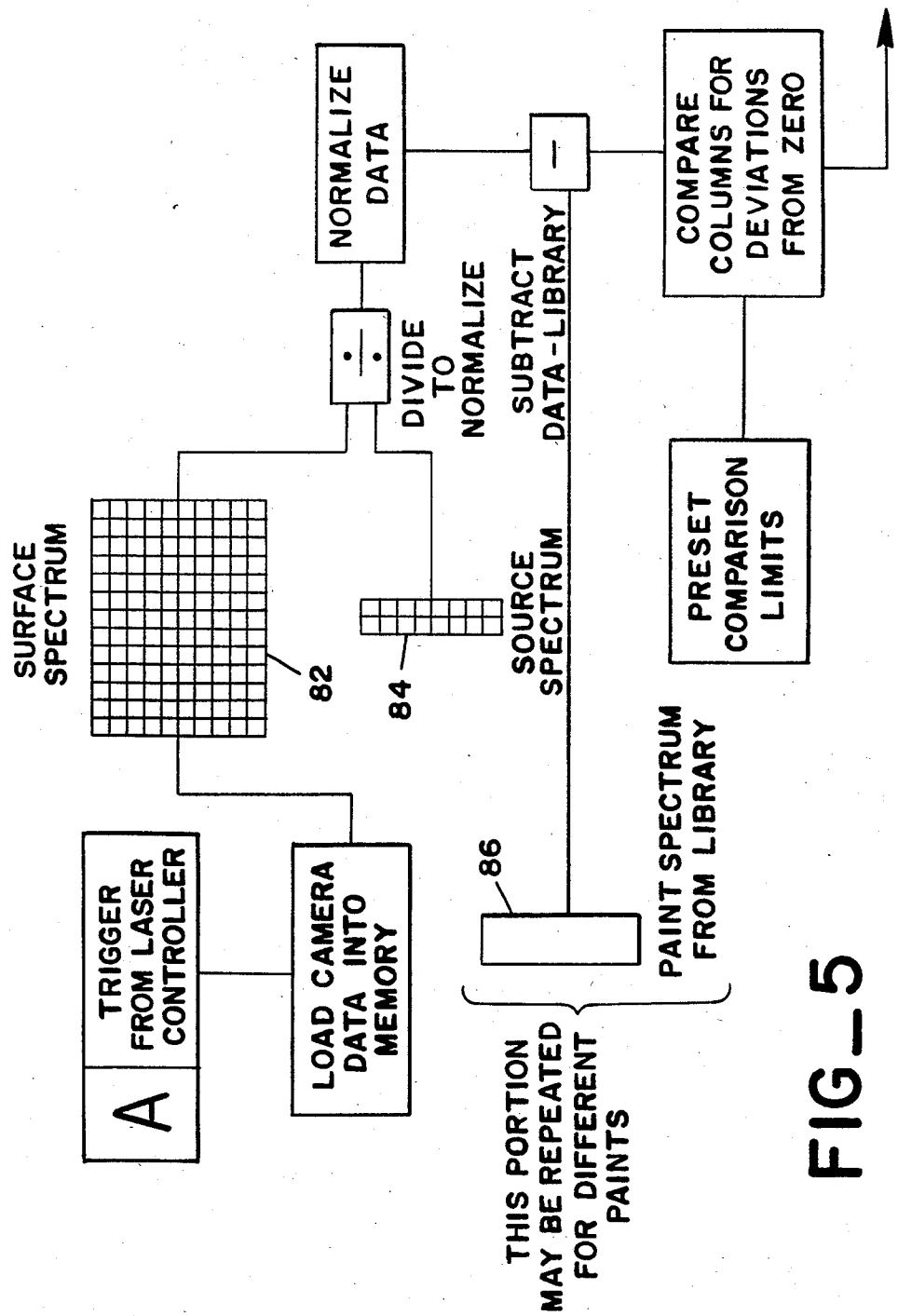
FIG_5

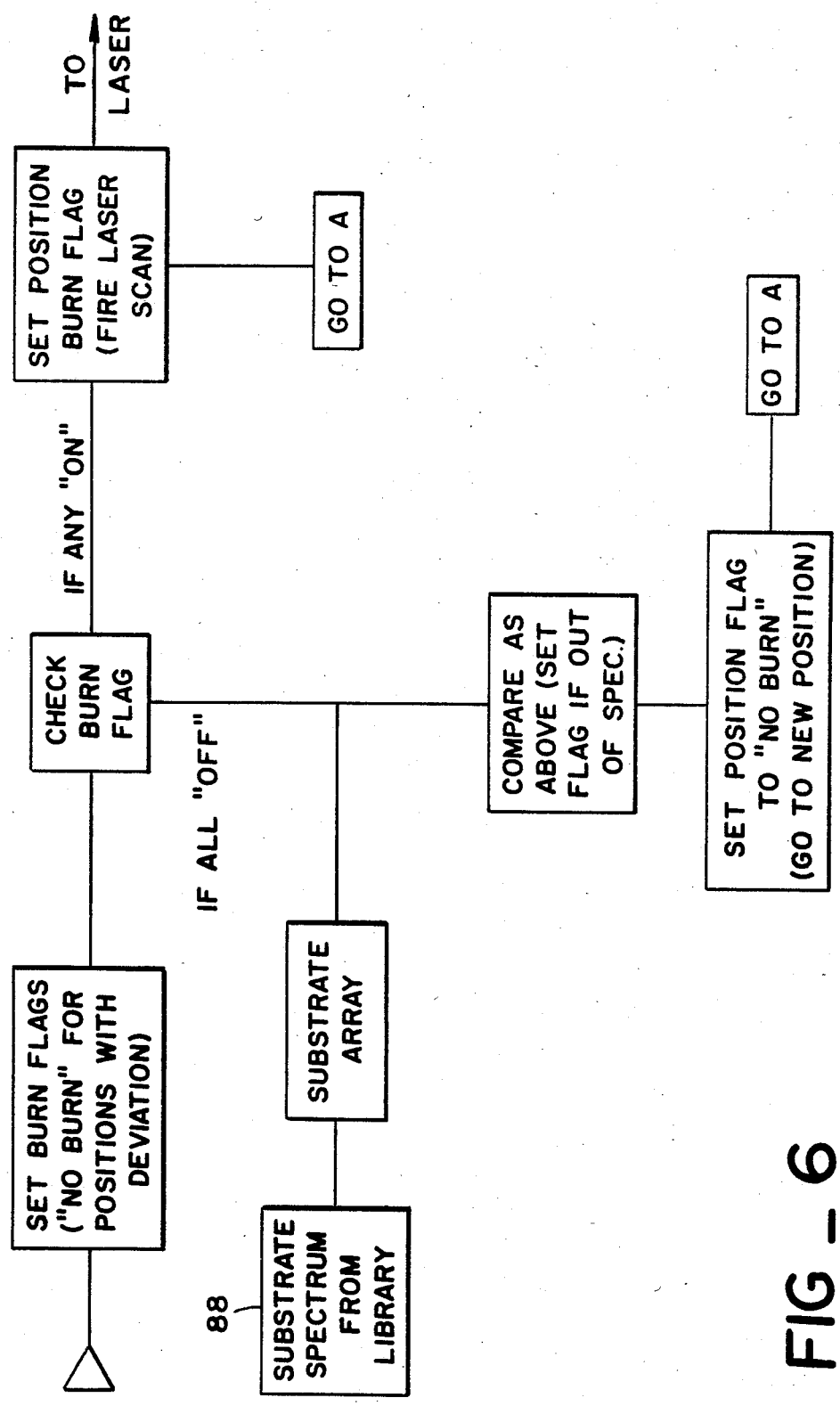
FIG_6

METHOD OF AND APPARATUS FOR THE REMOVAL OF PAINT AND THE LIKE FROM A SUBSTRATE

GOVERNMENT RIGHTS

The Government has rights in this invention pursuant to Contract No. N00014-82-C-2396 awarded by the U.S. Navy.

BACKGROUND OF THE INVENTION

1. Field of the Invention

This invention relates to the use of radiant energy for the removal of paint and the like from metal, wood, synthetic or composite substrates and more particularly to an improved method and apparatus for the control of the removal process.

2. Description of the Prior Art

Conventional Techniques for the removal or "stripping" of paint and the like include manual scraping, mechanical grinding, blasting with sand or other abrasives and the use of chemical strippers. All of such techniques are costly in terms of labor or materials or both. In addition, all of such techniques tend to generate a substantial waste product which must be disposed of and which, at least in the case of chemical strippers, may be a toxic waste requiring special disposal procedures.

More recently, the intense radiant energy provided by lasers and arc lamps has been used to remove paint and other coatings from metallic substrates with good results. The $CO_2$ laser, for example, operates at 10.6 micron wavelength which couples well to painted surfaces. The laser beam may be precisely controlled in terms of both power and position. The power of the laser may be selected to remove a top surface only of the paint by vaporization, thus requiring repeated pulses to remove the full depth of the paint layer. In addition, the position of the laser beam can be selectively programmed to remove paint only from certain areas leaving adjacent areas untouched. The vaporized paint may be easily removed in its gaseous form. To avoid degradation of the substrate due to heat, the laser beam may be pulsed at a low rate or moved through a raster over a large area thus allowing an individual area to cool between intervals when it is subjected to the laser beam. The exact nature of the raster and the exact number of pulses required to remove a layer of paint depends on system parameters such as the power of the laser, the size of the laser beam, the thickness of the paint, and the type of substrate upon which it is deposited. Where the substrate is aluminum, laser paint stripping has been carried out with good results because laser energy at 10.6 microns wavelength does not couple well to aluminum and the aluminum in fact acts as a mirror reflecting the energy away when all of the paint has been removed.

However, all of the above stripping techniques, including lasers, have only limited success on composite substrates such as carbon epoxy materials or other plastic reinforced materials. Such plastic reinforced materials are susceptible to mechanical damage and will be attacked by most chemical strippers. In addition, laser energy at 10.6 micron wavelength couples more efficiently to such materials than it does to the paint itself thus providing the potential for serious damage to the substrate by the laser beam.

Aircraft bodies, for example, now include substantial portions of carbon epoxy materials and are painted for a variety of reasons, including aesthetics, identification, camouflage, and performance. Such paint deteriorates under the action of weather and the mechanical forces to which the aircraft is subjected in use thus requiring periodic refurbishment. Often, the deteriorated paint is simply covered up by a new coat and many layers of paint may be built up before paint stripping is required. However, during the service life of an aircraft, many complete paint strippings are necessary. Prior to any such stripping the aircraft will not have a uniform coating of paint. Instead it may have several layers of paint in one spot and only one layer in others. The paint may be five to ten times thicker in some areas due to decals, insignias or other markings on the aircraft and in other areas it may have a hatch cover, underlying repair, or special materials under the paint. All of the above problems complicate the removal of paint from the aircraft and make it impossible to automate the paint removal process according to the teaching of the prior art.

The objects of this invention include the control and automation of the removal of paint and the like from a substrate without damage to the substrate.

SUMMARY OF THE INVENTION

According to the method and apparatus of this invention, the removal of paint and the like from the surface of a substrate includes impinging light having a given spectral range on a given area of the free surface of the paint and the like. The portion of the light which is reflected from the given area of paint and the like is subjected to spatial spectral dispersion. Such spatial spectral dispersion is electronically sensed and an electronic signal representative of such spatial spectral dispersion is generated. A reference electronic signal representative of a given spatial spectral dispersion of light within said given spectral range is electronically stored. The generated electronic signal is electronically compared with the reference electronic signal and if a substantial match is obtained, a high intensity beam of radiant energy is impinged on such given area of paint for a given period of time. The beam of radiant energy has a wavelength and power density sufficient to vaporize only a surface portion of such given area of paint and the like in the given period of time. The electronic signal generated after the impingement of the laser beam is again compared to the reference electronic signal and the alternate impingement of the laser beam and comparison of the generated electronic signal and reference electronic signal are repeated until such comparison results in a substantial mismatch at the end of a period of time during which the high intensity beam of radiant energy is impinged upon such area of paint and the like.

BRIEF DESCRIPTION OF THE DRAWING

This invention will be more fully understood from a reading of the following detailed description of preferred embodiments thereof in conjunction with the appended drawing wherein:

FIG. 1 is a conceptual drawing showing the physical arrangement of the optically active elements of applicants' method and apparatus.

FIG. 2 is a conceptual drawing of one optically active element of applicants' method and apparatus.

FIG. 3 is a conceptual drawing of a modification of FIG. 2.

FIG. 4 is a general block diagram of the electronic elements according to a preferred embodiment of applicants' method and apparatus.

FIG. 5 is a detailed block diagram of a portion of FIG. 4.

FIG. 6 is a detailed block diagram of the remainder of FIG. 4.

DETAILED DESCRIPTION OF PREFERRED EMBODIMENTS

Referring to FIG. 1, a laser 10 is shown with the beam 12 of radiant energy generated thereby impinging upon the surface 14 of a target. According to this invention, the surface 14 of the target is a layer of paint and the like on a substrate of metal, wood, graphite, epoxy, plastic, plastic reinforced material, etc. Although the embodiments of this invention described hereinafter utilize a laser to generate the beam of radiant energy 12, it should be understood that other sources of high intensity radiant energy such as focused arc lamps, for example, could be used. A transparent shield 16 of quartz, for example, is interposed between the target 14 and the apparatus of this invention in order to protect such apparatus from the materials removed from the target by the action of the beam 12 of radiant energy.

For paint removal the laser 10 is preferably a $CO_2$ laser which produces radiant energy having a 10.6 micron wavelength with high efficiency. Most paints will absorb radiant energy at 10.6 micron wavelength and the high efficiency of a $CO_2$ laser makes high power systems economically feasible.

$CO_2$ lasers are available with either pulsed or continuous outputs. Using a pulsed output for paint removal allows examination of the target before, between and after pulses for process control. It has been found that more than two and as many as ten $CO_2$ laser pulses having an energy density of about five joules per square centimeter and a pulse length of about twenty microseconds are required to vaporize the full thickness of a normal layer of paint depending upon the paint composition and the substrate to which it is applied. This removal rate is considered reasonable although the optimum conditions may vary. If the energy density and/or the pulse length is reduced, more pulses will be required to vaporize the full depth of a given layer of paint but finer control of the process will be possible. If the energy density and/or the pulse length is increased, fewer pulses will tend to be required to remove the full depth of a given layer of paint. However, pulses of higher energy density may break down the air above the paint surface inhibiting paint removal by absorbing energy from the beam and in any event, the control of the process will be more coarse.

The actual removal rate at a given pulse rate and energy density will be determined by the beam size (footprint area). For a given laser, the energy density selected will determine the size of the footprint area and the average power of the laser will determine the maximum pulse rate. Thus, assuming a laser capable of 4 kw average power and an energy density of about 5 joules per square centimeter, the footprint area would be about 1 square centimeter and the maximum pulse rate would be about 1000 Hz. Such a laser is typical of commercially available or buildable units.

The realized laser pulse rate and thus the achieved removal rate is determined by several items other than the maximum laser pulse rate. These limits include substrate heating, and smoke and residue clearing, as well as control factors.

Substrate heating appears to be the most serious limitation. The substrate heating rates will differ with both footprint area and substrate material. However, as will be more fully discussed hereinafter, substrate heating may be reduced by rastering of the laser beam and applicant's invention is specifically adapted to accommodate such rastering. In other words, the laser beam need not be repeatedly pulsed at a single location but may be moved after each pulse to an adjacent location to define a raster. The beam would return to a given location only after five or ten pulses thus giving each location five or ten times longer to cool before the beam is again impinged thereon. Such rastering allows a much higher pulse rate and the average removal time may be five or ten times as fast as the removal rate attainable by repeatedly impinging the beam at a given location.

The method and apparatus of applicants' invention is based on the fact that the vaporization of increments of a layer of paint and the like through the use of a high intensity beam of radiant energy will not substantially alter or discolor the remaining increments of the layer of paint and the like. This is believed to be due to the extremely high concentration of energy in the increment vaporized, the short time interval involved and the rapid dissipation of heat through vaporization, convection and conduction so that adjacent increments of the paint layer are not heated to a sufficient level to cause the alteration or discoloration thereof.

Thus, referring to FIG. 1, the basic optical elements of the method and apparatus of applicants' invention are shown. In order to promote a basic understanding of applicants' method and apparatus, it will be assumed that the beam 12 of the laser 10 provides a footprint of one square centimeter having an energy density of five joules per square centimeter. It will further be assumed that the laser 10 is capable of providing twenty microsecond pulses at a maximum pulse rate of about 1000 Hz.

According to applicants' invention, the surface 14 of the target is illuminated by an appropriate source of light 20 which may be a quartz halogen lamp 22 provided with an appropriate reflector 24. The reflector 24 need not focus the light from the lamp 22 only on the one square centimeter footprint of the beam 12 but may flood the footprint together with a substantial surrounding area.

An objective lens system 30 is mounted in tandem with the laser 10 and focuses an image of the one square centimeter footprint area of the beam 12 onto the entrance aperture 32 of an imaging spectrometer comprising an anastigmatic flat field holographic grating 34 and a focal plane array detector 36. The anastigmatic flat field holographic grating 34 provides an image of the entrance aperture 32 on the focal plane array 36 such that position in the aperture 32 and wavelength will be truly orthogonal in the image on the focal plane array. Several such gratings are available commercially and the grating chosen for use in an actual reduction to practice of this invention was manufactured by Jobin Yvon Division of Instruments, S' with 200 mm curvature, f/3 and 125 lines/mm. The spectral coverage of the system depends on the grating dispersion and focal length and on the length of the focal plane array. The grating chosen has a dispersion of about 80 nanometers per millimeter thus giving a coverage of 256 nanometers or the approximate region 450 to 700 nanometers.

Many focal plane arrays are currently available commercially. Silicon arrays have the best response for operation in the 400 to 800 nanometer spectral region. Most arrays are designed to operate only at the commercial TV rate of 32 milliseconds per frame. However, a series of specialized arrays manufactured by Reticon Corporation utilize an external clock which may be run very much faster than commercial TV rates. Lawrence Livermore National Laboratories has developed a series of cameras using these arrays which read out an entire frame in about one millisecond. Thus a Lawrence Livermore National Laboratories camera was selected for use as the focal plane array 36 in an embodiment of this invention.

It will be understood that as shown in FIG. 1, the light from the light source 20 which is reflected from the one square centimeter footprint area of the beam 12 will be focused by the lens system 30 through the aperture 32 onto the grating 34 which will provide a spatial spectral dispersion of such light along the length L of the focal plane array 36. Basically, the focal plane array comprises a plurality of individual silicon light sensor elements arranged in columns along the length L thereof. The image of the one square centimeter footprint area focused on the focal plane array may cover one or more column of the silicon sensor elements. According to the embodiment shown in FIG. 1, the spatial spectral dispersion of the image of the one square centimeter footprint area is distributed over three columns along the length L of the focal plane array ranging from the red at one end of the length L of the array to the blue at the other end of the length L of the array 36.

The focal plane array 36 is a self-scanning device in which the silicon sensor elements of each column are scanned from one end to the other to produce an electronic signal in which time is representative of wavelength and electrical output at a given point in time is representative of the intensity of the light at a particular wavelength. Thus the electronic signal output of the focal plane array may be coupled to an appropriate control device which is preferably a microprocessor having memory capability as will be more fully described hereinafter.

The basic operation of applicants' method and apparatus is as follows with reference to FIG. 1. Light from the light source 20 impinges upon the surface 14 of the target including at least the area to be impinged by the footprint of the beam 12 of the laser 10. With the laser 10 turned off, the lens system 30 will focus an image of the footprint area through the aperture 32 onto the grating 34. The grating 34 will produce a spatial spectral dispersion of the image on the focal plane array 36. The focal plane array 36 will produce an electronic signal representative of the spatial spectral dispersion of light thereon which spatial spectral dispersion will be characteristic of the color of the paint on the surface 14 of the target. Such electronic signal will be recorded in the memory of the control unit and the laser 10 will be actuated to produce a pulse of radiant energy in a beam 12 impinging upon the footprint area. At the end of the laser pulse the silicon elements of the focal plane array 36 will again be scanned to generate a new electronic signal which will be coupled to the control unit for comparison to the electronic signal previously recorded in the memory thereof. If the comparison results in a substantial match between the previously recorded electronic signal and the newly generated electronic signal, the laser 10 will again be actuated to produce a pulse of radiant energy. The above process would be repeated until some substantial mismatch is found between the newly generated electronic signal and the electronic signal originally stored in the memory of the control device. When such a mismatch occurs, further actuation of the laser 10 will be discontinued.

In order to avoid spurious readings and signals which may result due to changes in the spectral content of ambient light impinging upon surface 14 of the target, a fiber optic system 40 is preferably connected between the light source 20 and the aperture 32. Thus, a lens 42 couples light from the lamp 22 to a fiber optic cable 44. The fiber optic cable extends to a point immediately adjacent the aperture 32 thus light from the lamp 22 is transmitted through the fiber optic system 40 and impinges upon the grating 34 immediately adjacent the image of the footprint area. The grating 34 produces a spatial spectral dispersion of the light from the fiber optic system 44 on the focal plane array and the focal plane array may include a fourth column of silicon sensors to generate an electronic signal representative of the spectral content of the light from the lamp 22. Such electronic signal may be coupled to the control system and used for normalization of the electronic signals representative of the image of the footprint area. Thus any spectral content of the image of the footprint area introduced by ambient light can be abstracted during the comparison process.

Since the comparison can be made in about one millisecond, the pulse rate of the laser 10 may approach 1000 Hz. At a high pulse rate, the substrate of the target beneath the footprint of the beam 12 on the surface 14 may tend to be overheated and, furthermore, the center of the footprint of the beam 12 on the surface 14 will tend to be vaporized more deeply than the edges of the footprint on each pulse due to residual heating effects. It is for this reason that the image of the footprint is spread over three columns of the array of silicon sensors in the focal plane array. Thus the resolution of the focal plane array is finer than the footprint area so that differences in the spatial spectral dispersion across the footprint may be detected in order to avoid a burn-through at the center of the footprint area. It will be understood that if the spatial spectral dispersion detected at any one of the three columns fails to match the prerecorded spatial spectral dispersion, the laser 10 will not be actuated.

As mentioned hereinabove, overheating of the substrate may be avoided by moving the beam 12 through a raster. Such rastering of the beam 12 can also be used to minimize the effects of the uneven removal of paint in each footprint area.

Referring to FIG. 2, applicants' method and apparatus may be easily adapted for rastering of the beam 12 of the laser 10. It is noted that focal plane arrays of the type referred to hereinabove are available in various sizes, such as thirty-two columns of thirty-two silicon sensors each, fifty columns of fifty silicon sensors each, one hundred columns of one hundred sensors each and larger. In an actual embodiment of this invention an array having thirty-two columns of thirty-two sensors each was found to provide sufficient resolution as well as the fastest data reduction time. This is because the thirty-two by thirty-two element array can be scanned in one millisecond whereas it would take 2.5 and 10 milliseconds, respectively, to scan the fifty by fifty and one hundred by one hundred arrays.

FIG. 2 shows a preferred modification of the apparatus of FIG. 1 to adapt it for use of the thirty-two by thirty-two element focal plane array in accommodating the rastering of the laser beam. Thus as shown in FIG. 2 the aperture 32 is modified to take the form of an elongated slit 50. A lens system 52 is provided to focus an image of an area 53 of the surface 14 of the target which is ten centimeters long by one centimeter wide on the slit 50. The focal adjustments of the apparatus are such that the entire image of the area 53 is focused on the grating with the light from each square centimeter unit of the area 53 being dispersed over three adjacent columns of the sensors of the focal plane array. Thus the focal plane array is capable of producing thirty independent electronic signals, three for each square centimeter of the image area 53.

FIG. 3 of the drawing merely illustrates that the modification of the apparatus as shown in FIG. 2 may be easily adapted to accommodate a laser beam footprint larger than one square centimeter by using a lens system 54 including an auxiliary cylindrical focusing element 55. Thus the lens system 54 will focus an area 56 of the surface 14 of the target which may be ten centimeters wide by ten centimeters long, for example, on the same slit 50.

If the apparatus is modified as shown in FIG. 3 then a larger number of columns of the focal plane array will correspond to each footprint area of the laser beam. However, the operation of the apparatus will otherwise correspond to the following description of the operation of the apparatus according to the modification shown in FIG. 2.

It will be understood that the fiber optic cable 44 of the fiber optic system 40 shown in FIG. 1 will conduct light from the light source 20 to one end of the slit 50. Thus the light from the fiber optic cable 44 will be subjected to spatial spectral dispersion by the grating 34 and distributed over two columns of the silicon sensors at one side of the focal plane array. The remaining thirty columns of the focal plane array will thus be available for spatial spectral dispersion of the light from the area 53 with each one centimeter square unit of the area 53 being distributed over three adjacent columns of the focal plane array as described in connection with the one square centimeter footprint of FIG. 1.

Referring to FIG. 4 a thirty-two by thirty-two element focal plane array is represented at 60. It will be understood that the focal plane array 60 is physically mounted for movement together with the grating 34, slit 50, lens system 30, light source 20, laser 10 and shield 16. Such entire assembly can be built in a unit having a volume of less than one-half cubic foot and would weigh about ten pounds. The unit could be carried by a robotic arm or other movable structure and should be between one-half and one and one-half meters from the surface 14 of the target in use. The laser beam would be substantially normal to the surface 14 of the target with the light source 20 and lens system 30 nearly normal to the surface 14 of the target.

As will be described more fully hereinafter according to this embodiment of the apparatus of FIG. 1 modified as shown in FIG. 2, the beam 12 of the laser will be deflected to cover the area 53 in a raster. Thus the one square centimeter footprint of the beam 12 will be sequentially pulsed from left to right, for example, over the area 53 with each footprint impinging on a successive area. Other scanning sequences could be used and, if the laser has sufficient power, it could be operated continuously during a continuous raster over the area 53. Thus the laser 10 will include an appropriate mirror system or other means for deflecting the beam 12 to cover the area 53 in one square centimeter increments.

Referring again to FIG. 4, the focal plane array 60 as well as the laser are connected by means of electrical/electronic cables to a controller 62 which may be at a remote location. As discussed hereinabove in connection with the focal plane array 36, the focal plane array 60 is a self-scanning unit producing thirty-two electronic signals, each representative of the state of the silicon sensor elements of a column of the array. The structure of the controller is based on an LSI-11/30 microprocesser 64 manufactured by Digital Equipment Corporation and an Analogic AP 445 array processor 66 manufactured by Analogic Corporation. The controller 62 includes an electronic memory bank 68 capable of storing electronic signals for comparison with electronic signals generated by each column of the focal plane array.

Thus the controller 62 takes the electronic signals generated by each column of the focal plane array and determines whether the laser should be actuated for each one square centimeter unit of the area 53 of the surface 14 of the target. To this end, the controller 62 includes an array controller 70 which causes the electronic signal generated by each column of the focal plane array 60 to be coupled to the data bus 72 of the controller 62 through a 2.5 MHz eight-bit digitizer 74 and an appropriate interface 76. The microprocessor 64 and array processor 66 are programmed to compare the signals generated by each column of the focal plane array with reference signals stored in the memory 68. The result of such comparison with each group of three adjacent columns of the focal plane array is recorded by a flag register 78.

The status of the flag register 78 is communicated to the laser 10 through an appropriate interface 80 to control each raster of the footprint of the laser beam over the area 53. Thus there are ten flags, one for each one square centimeter beam footprint unit of the area 53. The logic used by the controller is based on the requirement of recognition of the paint to be removed. Thus the paint must be recognized by a matching comparison of electronic signals before a flag is set to actuate the laser for the unit area involved. If at any time during the process the paint is not recognized, the flag is not set and the laser will not be actuated for that particular unit area.

In operation, a given area 53 will be analyzed by the controller 62 as described hereinabove to set the flag register. While the laser is scanning the area 53, the controller 62 may be scanning an adjacent area 53 to re-set the flag register for that area.

Referring to FIGS. 5 and 6, the function of a preferred embodiment of this invention is shown in block diagram form. Upon initial start-up and at the end of each laser pulse according to such embodiment, a trigger signal is applied to point A (FIG. 5). The trigger signal causes the electronic signals from each column of the focal plane array to be loaded into the memory 68 at a given locationas indicated by the array symbol 82. Under the control of the array controller 70 and the processers 64, 66 the two columns of the thirty-two by thirty-two focal plane array on which the spectrum of the light source 20 is imaged through the fiber optic system 40 are recorded at a different location in the memory 68 in composite form as indicated by the symbol 84. Each of the electronic signals corresponding to a column of the focal plane array is then divided by the composite signal of the source spectrum 84 to normalize such signal for deviations introduced by ambient lighting conditions.

According to this embodiment of the invention, one or more electronic signals each representative of the spectrum of a paint as sensed by the focal plane array when illuminated by the light source are stored in a further part of the memory 68 as represented by the symbol 86. Such electronic signal is then subtracted from the normalized electronic signal obtained from the selected column of 82 and divided by the source spectrum signal. If the two electronic signals are the same, the resultant will be zero. An adjustable tolerance about zero may be provided by preset comparison limits selected to compensate for fading, wear and dirt. It will be understood that all of the above functions are provided by the microprocesser 64 and array processor 66.

If a matching condition is found as indicated by a zero signal, a "burn flag" will be set for that particular one square centimeter footprint unit of the area 53 as indicated at the upper left in FIG. 6. If a deviation from zero beyond the pre-set comparison limits is found, the burn flag will not be set.

The microprocesser 64 will then check the flag register 78 and if any burn flags are found, it will set a flag to trigger the laser beam raster for the particular area 53. At the same time, a trigger signal will be generated at point A to repeat the analysis for the next area 53 which may be located immediately under and adjacent the prior area 53, for example.

According to this embodiment of the invention, an electronic signal representative of the spectrum of the substrate or of a primer paint or both may be stored in yet further locations of the memory 68. Thus if no burn flag is found upon checking the flag register for any given area 53, the microprocessor 64 will cause the electronic signal representative of the substrate and/or primer spectrums to be subtracted from the signal for each column of the focal plane array. If a zero signal is obtained, it will indicate that the substrate or primer has been exposed. If a deviation from zero beyond a pre-set comparison limit results, then a further flag will be set which may be stored for further manual or automatic processing. Again, a trigger signal is generated at point A to repeat the process for the next area 53.

It will be understood that each area 53 will be repeatedly scanned in whole or in part according to a raster pattern established by the microprocessor which will control the position of the laser 10 at the beginning of each scan. Such scanning will be repeated until every area 53 of the raster scan pattern fails to result in a burn flag.

It will also be understood that applicants' controller is specifically compatible with robotics technology. Thus applicants' method and apparatus may be integrated into a robotic system for controlling the position of a laser in connection with a particular painted substrate for the removal of the paint therefrom. It is believed that those skilled in the art will make obvious modifications in applicants' method and apparatus as described hereinabove without departing from the scope of the following claims.

What is claimed is:

1. The method of removing paint and the like from the surface of a substrate comprising the steps of:
   (a) impinging light having a given spectral range on a given area of the free surface of said paint and the like;
   (b) subjecting the portion of said light which is reflected from said given area of said paint and the like to spatial spectral dispersion;
   (c) electronically sensing said spatial spectral dispersion and generating an electronic signal representative of said spatial spectral dispersion;
   (d) electronically storing a reference electronic signal representative of a given spatial spectral dispersion of light within said given spectral range;
   (e) electronically comparing said electronic signal with said reference electronic signal and, upon said comparison resulting in a substantial match between said electronic signal and said reference electronic signal, impinging a high intensity beam of radiant energy on said given area of said paint and the like for a given period of time, said beam of radiant energy having a wavelength and energy density sufficient to vaporize only a surface portion of said given area of said paint and the like in said given period of time;
   (f) after said given period of time again electronically comparing said electronic signal with said reference electronic signal and again impinging said beam of radiant energy on said given area of paint and the like for said given period of time only upon said electronic comparison resulting in a substantial match between said electronic signal and said reference electronic signal, and
   (g) repeating step f) until said electronic comparison results in a substantial mismatch between said electronic signal and said reference electronic signal.

2. The method of claim 1 including the steps of:
subjecting a portion of said impinging light having said given spectral range to spatial spectral dispersion, electronically sensing said spatial spectral dispersion and generating an electronic signal representative of said spatial spectral dispersion of said impinging light having said given spectral range; and
utilizing said electronic signal representative of said spatial spectral dispersion of said impinging light having said given spectral range to normalize said electronic signal prior to comparing said electronic signal with said reference electronic signal.

3. The method of claim 1 including the steps of:
electronically storing a further reference electronic signal representative of a spatial spectral dispersion different from said given spatial spectral dispersion;
upon said electronic comparison resulting in a substantial mismatch between said electronic signal and said reference electronic signal further electronically comparing said electronic signal and said further reference electronic signal; and
upon said further electronic comparison resulting in a substantial match again impinging said beam of radiant energy on said given area of paint and the like for said given period of time.

4. The method of claim 3 including the step of:
actuating a signaling means upon said further electronic comparison resulting in a substantial mismatch.

5. The method of claim 3 including the steps of:
electronically storing yet another reference electronic signal representative of a spatial spectral dispersion which is not the same as said given spatial spectral dispersion and said different spatial spectral dispersion;

upon said further electronic comparison resulting in a substantial mismatch, still further electronically comparing said electronic signal to said yet another electronic signal; and upon said still further electronic comparison resulting in a substantial mismatch actuating a signaling means.

6. Apparatus for removing paint and the like from the surface of a substrate comprising:

(a) means for impinging light having a given spectral range on a given area of the free surface of said paint and the like;

(b) means for subjecting the portion of said light which is reflected from said given area of said paint and the like to spatial spectral dispersion;

(c) means for electronically sensing said spatial spectral dispersion and generating an electronic signal representative of said spatial spectral dispersion;

(d) means electronically storing a reference electronic signal representative of a given spatial spectral dispersion of light within said given spectral range;

(e) means for impinging a high intensity beam of radiant energy on said given area of said paint and the like for a given period of time, said beam having a wavelength and energy density sufficient to vaporize only a surface portion of said given area of said paint and the like in said given period of time;

(f) means electronically comparing said electronic signal with said reference electronic signal and actuating said means for impinging said beam on said given area of paint and the like for said given period of time only upon said electronic comparison resulting in a substantial match between said electronic signal and said reference electronic signal; and (g) means for actuating said means for electronically comparing said electronic signal with said reference signal both before and after each said given period of time during which said means for impinging said beam is actuated.

7. Apparatus as claimed in claim 6 including means extracting a light sample from said means for impinging light having a given spectral range on said given area;

means subjecting said light sample to spatial spectral dispersion;

means electronically sensing said spatial spectral dispersion and generating an electronic signal representative of said spatial spectral dispersion of said light sample; and means utilizing said electronic signal representative of said spatial spectral dispersion of said light sample to normalize said electronic signal prior to comparing said electronic signal with said reference electronic signal.

8. The apparatus of claim 6 wherein said means for subjecting the portion of said light which is reflected from said given area of said paint and the like to spatial spectral dispersion comprises a lens means imaging said given area through an aperture onto an anastigmatic flat field holographic grating.

9. The apparatus of claim 8 wherein said means for electronically sensing said spatial spectral dispersion and generating an electronic signal representative thereof comprises a planar array of a plurality of silicon light sensing elements located at the focal plane of said anastigmatic flat field holographic grating.

10. Apparatus as claimed in claim 9 wherein said means for impinging a high intensity beam of radiant energy on said given area of said paint and the like for a given period of time comprises a $CO_2$ laser providing a pulse of radiant energy at a wavelength of about 10.6 microns with an energy density of about five joules per square centimeter and a pulse length of about twenty microseconds.

* * * * *